United States Patent
Manrodt et al.

(10) Patent No.: US 6,445,952 B1
(45) Date of Patent: Sep. 3, 2002

(54) APPARATUS AND METHOD FOR DETECTING MICRO-DISLODGMENT OF A PACING LEAD

(75) Inventors: Christopher M. Manrodt, Blaine; H. Toby Markowitz, Roseville; Bradley C. Peck, Ham Lake, all of MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/573,507

(22) Filed: May 18, 2000

(51) Int. Cl.$^7$ ................................................ A61N 1/08
(52) U.S. Cl. ........................................................ 607/28
(58) Field of Search ................................. 607/28, 27, 2, 607/63; 600/547

(56) References Cited

U.S. PATENT DOCUMENTS

| | | | |
|---|---|---|---|
| 4,140,131 A | 2/1979 | Dutcher et al. | 128/419 |
| 4,245,643 A | * 1/1981 | Benzing et al. | 607/28 |
| 4,257,423 A | 3/1981 | McDonald et al. | 128/419 |
| 4,374,382 A | 2/1983 | Markowitz | 340/870.01 |
| 4,428,378 A | 1/1984 | Anderson et al. | 128/419 |
| 4,549,548 A | 10/1985 | Wittkampf et al. | 128/419 |
| 4,556,063 A | 12/1985 | Thompson et al. | 128/419 |
| 4,606,349 A | 8/1986 | Livingston et al. | 128/419 |
| 4,821,723 A | 4/1989 | Baker, Jr. et al. | 128/419 |
| 4,899,750 A | 2/1990 | Ekwall | 128/419 |
| 4,969,460 A | 11/1990 | Callaghan et al. | 128/419 |
| 5,003,975 A | 4/1991 | Hafelfinger et al. | 128/419 |
| 5,052,388 A | 10/1991 | Sivula et al. | 128/419 |
| 5,127,404 A | 7/1992 | Wyborny et al. | 128/419 |
| 5,131,388 A | 7/1992 | Pless et al. | 128/419 |
| 5,137,021 A | 8/1992 | Wayne et al. | 128/419 |
| 5,144,949 A | 9/1992 | Olson | 128/419 |
| 5,156,149 A | 10/1992 | Hudrlik | 128/419 |
| 5,158,078 A | 10/1992 | Bennett et al. | 128/419 |
| 5,184,614 A | 2/1993 | Collins et al. | 128/419 |
| 5,201,808 A | 4/1993 | Steinhaus et al. | 128/419 |
| 5,201,865 A | 4/1993 | Kuehn | 128/419 |
| 5,222,493 A | 6/1993 | Sholder | 128/419 |
| 5,312,453 A | 5/1994 | Shelton et al. | 607/19 |
| 5,314,430 A | 5/1994 | Brady | 607/5 |
| 5,350,410 A | 9/1994 | Kleks et al. | 607/28 |
| 5,354,316 A | 10/1994 | Keimel | 607/15 |
| 5,411,533 A | 5/1995 | Dubreuil et al. | 607/28 |
| 5,431,692 A | 7/1995 | Hansen et al. | 607/28 |

(List continued on next page.)

*Primary Examiner*—Kennedy Schaetzle
(74) *Attorney, Agent, or Firm*—Girma Wolde-Michael

(57) ABSTRACT

An apparatus and method for detecting micro-dislodgment at a heart tissue/pacing lead electrode interface involves measuring a first pacing threshold parameter at a first time in a patient's cardiac cycle and measuring a second pacing threshold parameter at a second time in the patient's cardiac cycle. Micro-dislodgment occurring at the heart tissue/pacing lead electrode interface is detected using the first and second pacing threshold parameters. Micro-dislodgment may be detected by comparing a difference between, or a ratio of, the first and second pacing threshold parameters to a preestablished maximum allowable deviation value. A difference between the first and second pacing threshold parameters or a ratio in excess of the preestablished maximum allowable deviation value indicates a problem at the heart tissue/pacing lead interface. The first and second pacing threshold parameters are preferably pacing threshold voltages, and the preestablished maximum allowable deviation value is either a voltage ranging from about 0.2 volts to about 2 volts or a percentage ranging from about 5% to about 100%. The micro-dislodgment procedure may be performed in-situ an implantable pulse generator (IPG), with data indicative of a detected change at the heart tissue/pacing electrode interface being stored in a memory coupled to the IPG and subsequently read out of memory for evaluation. Alternatively, the micro-dislodgment procedure may be performed using an external programmer and may further be performed during implantation of a pacing lead electrode at the heart tissue/pacing lead electrode interface to assure a physician of proper lead attachment.

40 Claims, 8 Drawing Sheets

U.S. PATENT DOCUMENTS

| | | | |
|---|---|---|---|
| 5,476,487 A | 12/1995 | Sholder | 607/28 |
| 5,480,414 A | 1/1996 | Stroebel et al. | 607/28 |
| 5,507,782 A | 4/1996 | Kieval et al. | 607/9 |
| 5,534,018 A | 7/1996 | Wahlstrand et al. | 607/27 |
| 5,545,186 A | 8/1996 | Olson et al. | 607/14 |
| 5,549,646 A | 8/1996 | Katz et al. | 607/8 |
| 5,549,652 A | 8/1996 | McClure et al. | 607/28 |
| 5,557,210 A * | 9/1996 | Cappa et al. | 324/538 |
| 5,601,615 A | 2/1997 | Markowitz et al. | 607/28 |
| 5,607,455 A * | 3/1997 | Armstrong | 607/8 |
| 5,683,431 A * | 11/1997 | Wang | 607/28 |
| 5,697,956 A | 12/1997 | Bornzin | 607/28 |
| 5,702,427 A | 12/1997 | Ecker et al. | 607/28 |
| 5,713,933 A | 2/1998 | Condie et al. | 607/28 |
| 5,718,720 A | 2/1998 | Prutchi et al. | 607/28 |
| 5,766,229 A | 6/1998 | Bornzin | 607/28 |
| 5,861,012 A | 1/1999 | Stroebel | 607/28 |
| 6,195,584 B1 * | 2/2001 | Hill et al. | 607/28 |
| 6,317,633 B1 * | 11/2001 | Jorgenson et al. | 607/28 |

* cited by examiner

APPARATUS AND METHOD FOR DETECTING MICRO-DISLODGMENT OF A PACING LEAD

FIELD OF THE INVENTION

This invention relates to the field of implantable medical devices and, more particularly, to detection of micro-dislodgment of a pacing lead electrode at a heart tissue/pacing lead electrode interface.

BACKGROUND OF THE INVENTION

Implantable pulse generators (IPG) are currently being used for cardiac pacemakers, defibrillator, and cardioverter applications. Such devices typically employ one or more pacing leads that connect the IPG with endocardial, epicardium or intravascular tissue using one or more electrodes coupled to the pacing leads. A pacemaker, for example, employs an IPG for purposes of pacing a patient's heart, and may perform critical functions without which the patient may die nearly immediately.

A problem common to such IPG devices concerns changes that may occur at the electrode/heart tissue interface which may adversely affect the transmission of electrical stimulating pulses needed to properly pace the heart. An unsatisfactory lead placement of the lead, for example, may negatively influence the ability of the lead to transmit energy between the IPG and heart tissue via the heart tissue/pacing lead electrode interface.

Several techniques have been developed to evaluate the heart tissue/pacing lead electrode interface. U.S. Pat. No. 5,003,975 to Hafelfinger et al. provides a good description of various prior art solutions, including those described in U.S. Pat. No. 4,140,131 to Dutcher et al.; U.S. Pat. No. 4,549,548 to Wittkampf et al.; and U.S. Pat. No. 4,606,349 to Livingston et al.; each of which is hereby incorporated by reference in its entirety. Prior art techniques involving sensing and using lead impedance for determining the adequacy of lead conductor connections to the heart may be found in U.S. Pat. No. 5,534,018 to Walhstrand et al; U.S. Pat. No. 5,201,865 to Kuehn; U.S. Pat. No. 5,201,808 to Steinhaus et al.; U.S. Pat. No. 5,156,149 to Hudrlik; U.S. Pat. No. 5,137,021 to Wayne et al.; U.S. Pat. No. 4,899,750 to Ekwall; U.S. Pat. No. 5,184,614 Collins; U.S. Pat. No. 5,350,410 to Kleks et al.; U.S. Pat. No. 5,431,692 to Hansen et al.; and U.S. Pat. No. 5,549,646 to Katz et al.; each of which is hereby incorporated by reference in its entirety.

Although some of the proposed techniques for evaluating the heart tissue/pacing lead electrode interface provide for the detection of gross problems, such prior art techniques are unable to detect subtle changes at the heart tissue/pacing lead electrode interface that may, over time, adversely affect the ability of the IPG to properly pace the heart.

Micro-dislodgment, for example, is generally understood as a failure mechanism which limits the ability of the pacing system to function properly in the patient. Micro-dislodgment may be viewed as a precursor to a serious or potentially catastrophic pacing failure condition. Micro-dislodgment is understood as an undesirable change occurring at the heart tissue/pacing lead electrode interface that adversely affects the ability of the IPG to cause depolarization via the heart tissue/pacing lead electrode interface. Micro-dislodgment is undetectable when visualized using available imaging technologies, such as a chest x-ray. It is important to appreciate that the ability to detect subtle undesirable changes at the heart tissue/pacing lead electrode interface (e.g., micro-dislodgment) well in advance of a significant or catastrophic failure condition provides a physician the opportunity to further test and evaluate a suspect lead placement and, if necessary, reposition, repair or replace a suspect lead prior to the occurrence of a potentially life threatening episode.

There exists a need for a method and apparatus for predicting and avoiding lead dislodgment. There exists a further need for such a method and apparatus that may be applied intraoperatively, at follow-up, or on an ambulatory basis.

SUMMARY OF THE INVENTION

The present invention is directed to an apparatus and method for detecting changes at a heart tissue/pacing lead electrode interface. In particular, the present invention is directed to an apparatus and method for detecting micro-dislodgment at a heart tissue/pacing lead electrode interface. The micro-dislodgment detection approach of the present invention may be employed to detect micro-dislodgment at a heart tissue/pacing lead electrode interface in any of the four heart chambers.

Detecting micro-dislodgment at a heart tissue/pacing lead electrode interface involves measuring a first pacing threshold parameter at a first time during a patient's cardiac cycle and measuring a second pacing threshold parameter during a second time during the patient's cardiac cycle. Measuring the first pacing threshold parameter involves measuring the first pacing threshold parameter after initiation of an atrial contraction but prior to any appreciable amount of ventricular contraction, such as after a delay of up to about 110 milliseconds (ms) subsequent to initiation of an atrial contraction. The second pacing threshold parameter is measured after initiation of an atrial contraction and after an appreciable amount of ventricular contraction, such as after a delay of about 100 ms to about 400 ms subsequent to initiation of an atrial contraction.

The first and second pacing threshold parameters are used to detect micro-dislodgment at the heart tissue/pacing lead electrode interface, such as by comparing a difference between the first and second pacing threshold parameters to a preestablished maximum allowable deviation value. A difference between the first and second pacing threshold parameters in excess of the preestablished maximum allowable deviation value indicates a problem at the lead electrode/heart tissue interface. In one embodiment, each of the first and second pacing threshold parameters is a pacing threshold voltage, and the preestablished maximum allowable deviation value is a voltage ranging from about 0.2 volts to about 2 volts or more.

Alternatively, detecting undesirable changes at a heart tissue/pacing lead electrode interface involves computing a ratio of the first pacing threshold parameter relative to the second pacing threshold parameter and comparing the computed ratio to a preestablished maximum allowable deviation value. A problem at the lead electrode/heart tissue interface is indicated by the computed ratio exceeding the preestablished maximum allowable deviation value. The preestablished maximum allowable deviation value is a percentage ranging from about 5% to about 100%.

The respective first and second measuring steps and the detecting step may be performed using an external programmer in cooperation with an implantable medical device or, alternatively, solely by the use of an implantable medical device comprising a pulse generator or with a pacing system analyzer or external pacemaker at time of implant. The respective first and second measuring steps and the detecting step may be performed during the implantation procedure of a pacing lead electrode at the heart tissue/pacing lead electrode interface. The respective first and second measuring steps and the detecting step may also be performed using an implantable medical device while the patient is ambulatory. Data indicative of micro-dislodgment may be stored in the implantable medical device and subsequently read out of memory at any time for evaluation by a physician.

An apparatus for detecting micro-dislodgment at a heart tissue/pacing lead electrode interface in accordance with an embodiment of the present invention includes an implantable medical device comprising a pulse generator and first and second pacing leads. In accordance with one embodiment of the present invention, a first electrode is coupled to the first pacing lead and is adapted for implantation in the right atrium of a patient's heart. A second electrode is coupled to the second pacing lead and is adapted for implantation in the right ventricle of the heart. A microprocessor determines an occurrence of micro-dislodgment at the second electrode/right ventricle interface using a first pacing threshold parameter determined for the right ventricle prior to any appreciable contracting of the right ventricle and a second pacing threshold parameter determined for the right ventricle during appreciable contracting of the right ventricle.

The microprocessor may determine an occurrence of micro-dislodgment at the second electrode/right ventricle interface by comparing a difference between the first and second pacing threshold parameters to a preestablished maximum allowable deviation value in a manner previously described. Alternatively, the microprocessor may determine an occurrence of micro-dislodgment at the second electrode/right ventricle interface by computing a ratio of the first pacing threshold parameter relative to the second pacing threshold parameter and comparing the computed ratio to a preestablished maximum allowable deviation value in a manner previously described. It is understood that a similar micro-dislodgment detection apparatus and methodology may be implemented for left ventricular implants.

The microprocessor provided in the implantable medical device may further store data indicative of a detected occurrence of micro-dislodgment in a memory coupled thereto. The microprocessor coordinates transferring of the stored data from the memory to an external programmer. Alternatively, the microprocessor that coordinates the micro-dislodgment evaluation may be provided in an external programmer.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
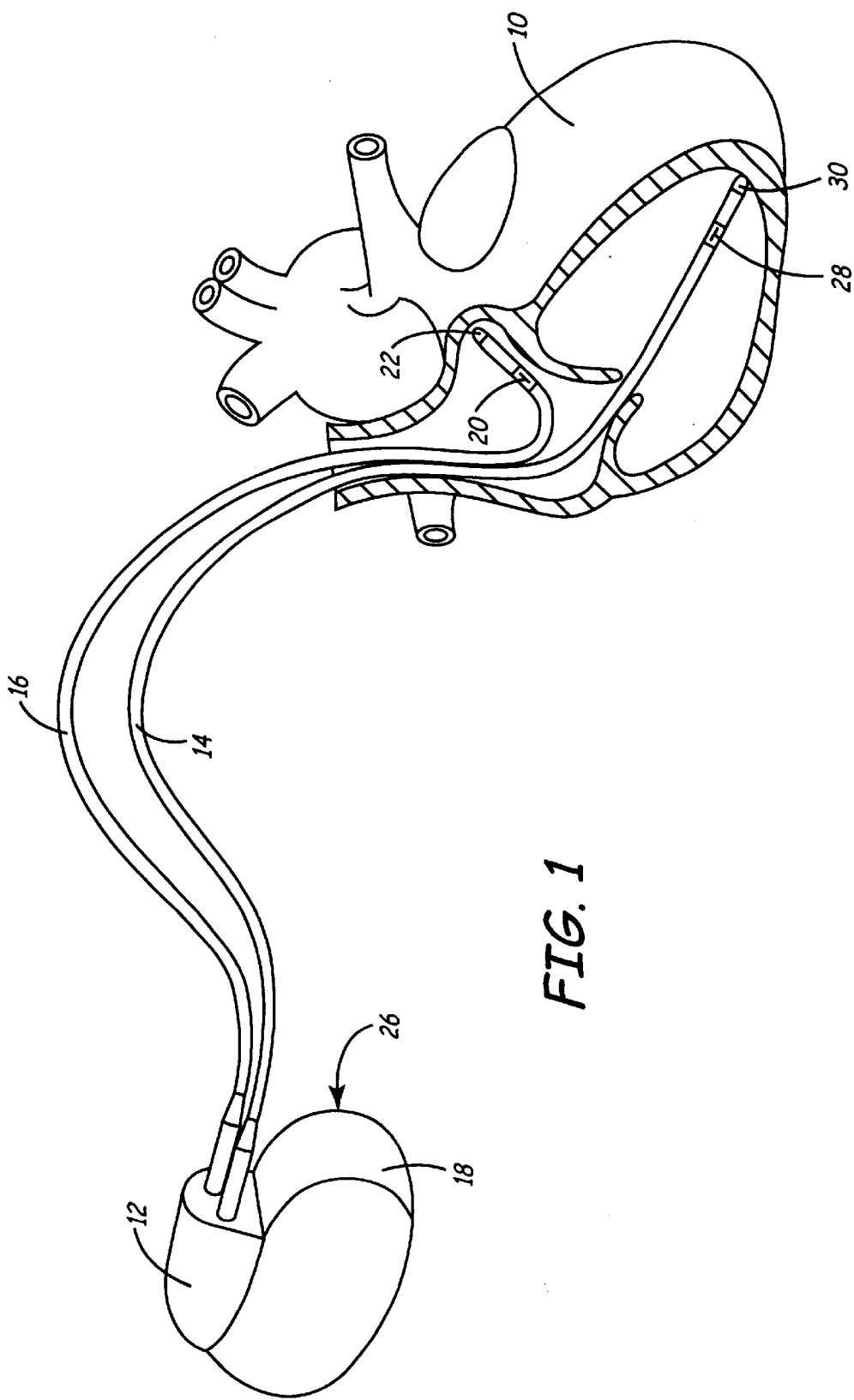
FIG. 1 is an illustration of a dual chamber pacemaker in conjunction with an associated set of cardiac pacing leads, illustrated as located in a cutaway view of a human heart, with which a pacing lead dislodgment detection methodology of the present invention may be practiced.

While the invention is amenable to various modifications and alternative forms, specifics thereof have been shown by way of example in the drawings and will be described in detail hereinbelow. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which is shown by way of illustration, various embodiments in which the invention may be practiced. It is to be understood that other embodiments may be utilized, and structural and functional changes may be made without departing from the scope of the present invention.

Figure 2:
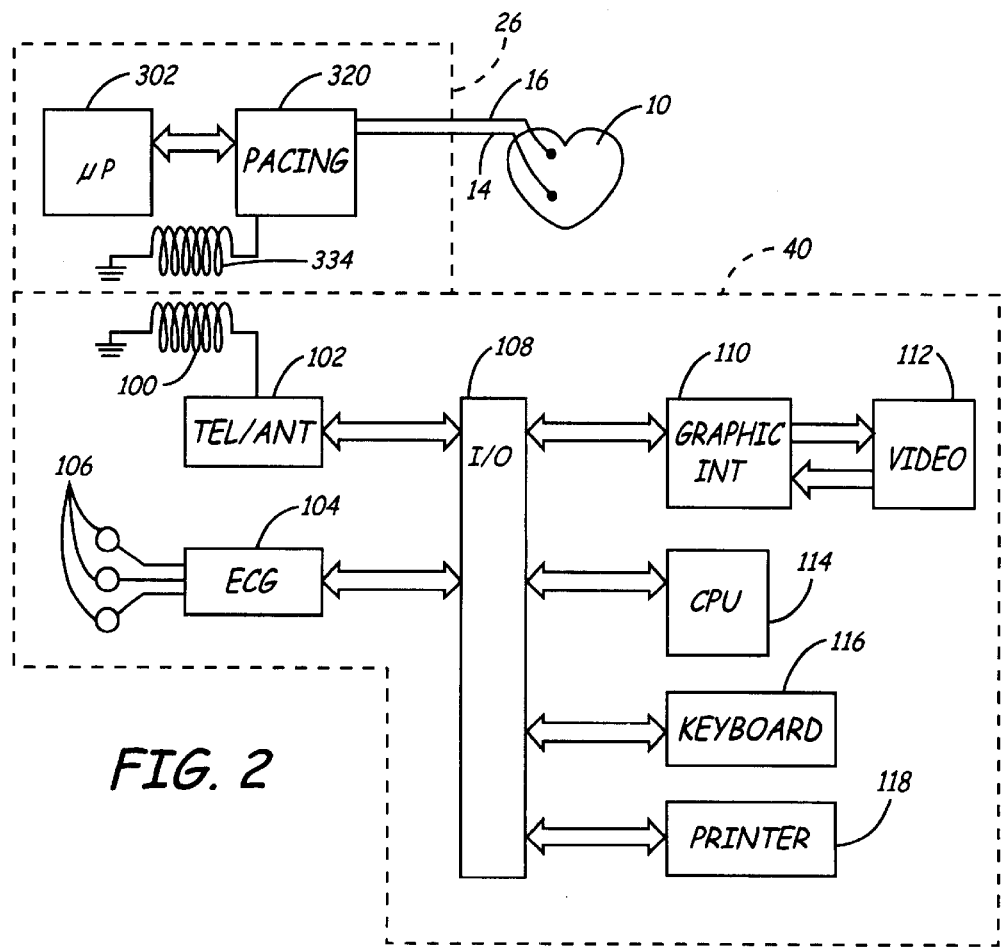
FIG. 2 is a functional block diagram of the dual chamber pacemaker illustrated in FIG. 1 in conjunction with an external programmer/monitoring unit, for use in performing a pacing lead dislodgment detection methodology in accordance with an embodiment of the present invention.
Figure 3:
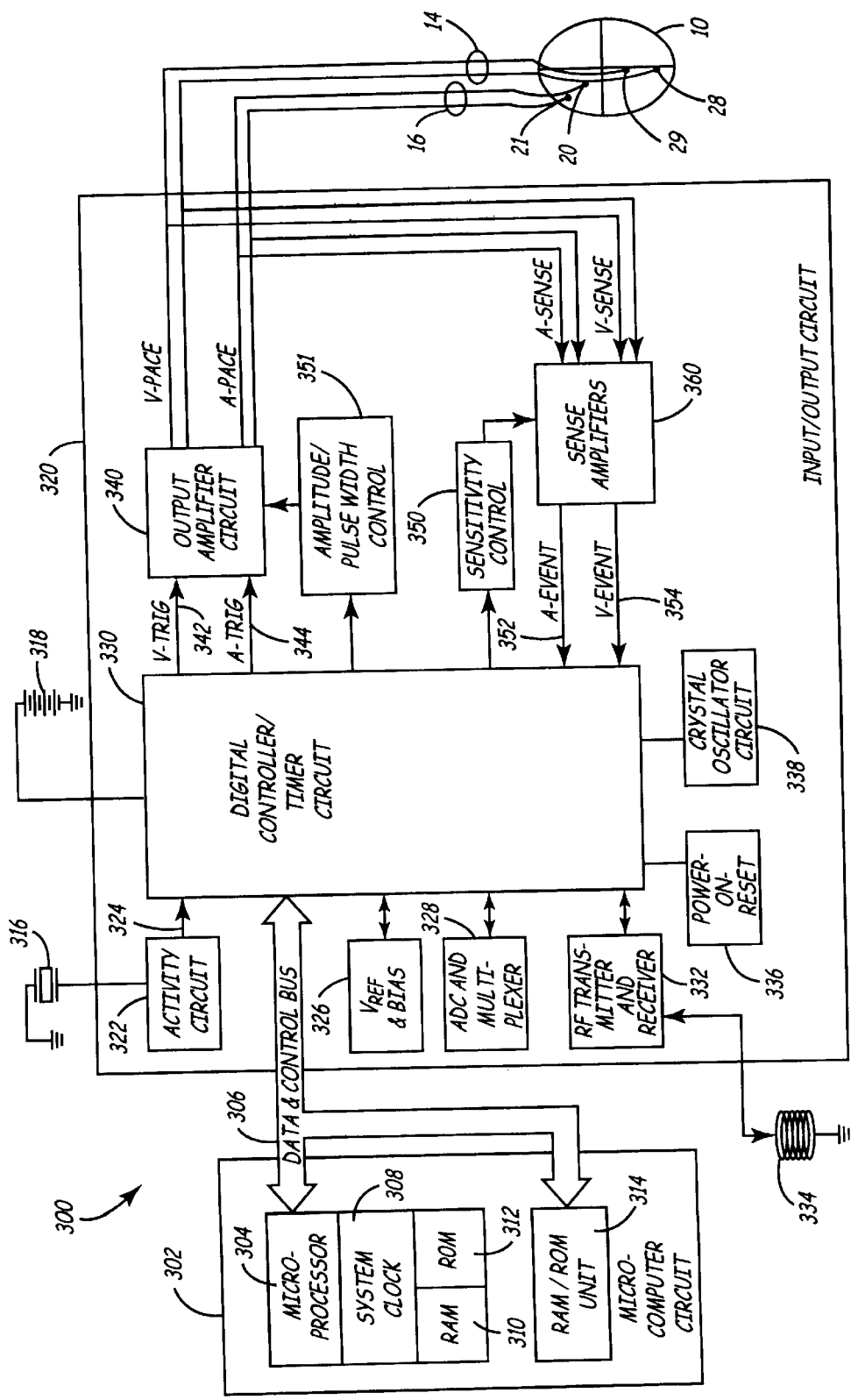
FIG. 3 is a block diagram of the dual chamber pacemaker illustrated in FIGS. 1 and 2, illustrating the functional components of the device in greater detail.

In accordance with a preferred embodiment, the inventive apparatus and methods of the present invention are incorporated into a dual chamber implantable pulse generator or IPG as illustrated in FIGS. 1–3. The following detailed description of a multi-programmable, rate responsive, dual chamber IPG and remote programmer provides a preferred mode in which various aspects of the present invention may be incorporated. It will be understood that other types of dual chamber pacemakers or pacing modes would selectively incorporate features of the particularly described IPG and programmer architecture as necessary.

FIG. 1 illustrates the external configuration of a dual chamber IPG 26, which is provided with a hermetically sealed enclosure 18, typically fabricated of biocompatible metal such as titanium. Mounted to the top of the enclosure 18 is a connector block assembly 12, which receives electrical connectors located on the proximal ends of leads 14 and 16. The combination of the leads 14 and 16 and the IPG 26 constitute an implantable pacemaker. FIGS. 1 and 2 are described in detail in U.S. Pat. Nos. 5,601,615 and 5,507,782, which are hereby incorporated by reference in their respective entireties.

Lead 16 is an atrial bipolar pacing lead, carrying two electrodes 20 and 22. Electrodes 20 and 22 are used both to sense atrial depolarizations (P-waves) and to deliver atrial pacing pulses. Atrial pacing pulses may be delivered between electrodes 20 and 22 in a bipolar pacing mode or between electrode 22 and the housing 18 of the IPG 26 in a unipolar pacing mode. Sensing of P-waves may occur between electrode 20 and electrode 22 in a bipolar sensing mode or between either of electrode 20 and 22 and the housing 18 of the IPG 26 in a unipolar sensing mode.

Similarly, lead 14 represents a ventricular bipolar pacing lead, carrying two electrodes 28 and 30. As discussed above in conjunction with atrial lead 16, electrodes 28 and 30 are used to sense and pace the ventricle. Bipolar ventricular pacing may be accomplished between electrodes 30 and 28 or unipolar ventricular pacing may be accomplished between electrode 30 and the conductive housing 18 of IPG 26. Sensing of ventricular depolarizations or R-waves may be accomplished between electrodes 30 and 28 in a bipolar sensing mode or between either of electrodes 30 and 28 and the housing 18 of the IPG 26 in a unipolar sensing mode.

FIG. 2 illustrates IPG 26 in block diagram form, coupled to a human heart 10 through the leads 14, 16, in conjunction with an external programmer 40 corresponding to those typically employed to program modern, multi-programmable implantable pacemakers. Within the housing of the IPG 26 are located the pacing circuitry 320, which includes circuitry for performing all of the basic timing, stimulation and sensing functions, and a microcomputer circuit 302, which controls the timing intervals provided by the pacing circuitry 320. Pacing circuitry 320 also includes a bi-directional telemetry circuit coupled to an antenna 334, allowing transmission of information from external programmer 40 into the IPG 26 to modify its parameters and allowing transmission of information from the IPG 26 to the external programmer 40, again generally corresponding to telemetry and programming systems presently existing in commercially marketed multi-programmable implantable pacemakers.

The programmer 40 also includes a telemetry antenna 100 coupled to a telemetry/antenna driver circuit 102 which serves to demodulate telemetry signals received from antenna 334 of the IPG 26, and to apply them in parallel or serial digital format to input/output (I/O) unit 108. The telemetry signals in turn may be applied to a video monitor 112, via graphic interface 110, and/or provided to central processing unit 114 and/or printer 118. Microprocessor 114 controls the operation of the programmer 40 and is responsive to physician entered commands via keyboard 116, for controlling programming signals sent to the IPG 26 and operation of the video display 112 and printer 118. Also illustrated in FIG. 2 is an ECG interface 104 coupled to three ECG electrodes 106 which are intended to be placed upon the patient's body. ECG interface 104 provides sensed electrograms to input/output device 108, where they in turn may be provided to the video display 112, the central processing unit 114 or the printer 118.

FIG. 3 is a more detailed functional block diagram of the pacemaker illustrated in FIGS. 1 and 2, as connected to a human heart 10. The combined IPG circuit 300 illustrated is located within the conductive housing 18 of the IPG 26 as illustrated in FIG. 1. The bipolar leads 14 and 16 are illustrated schematically as coupled directly to the input/output circuit 320. However, in the actual implantable device they would, of course, be coupled by means of removable electrical connectors inserted in the connector block 12 illustrated in FIG. 1.

The IPG circuit 300 is divided generally into a microcomputer circuit 302 and a pacing circuit 320. An output amplifier circuit 340 includes a ventricular pulse generator circuit coupled to the ventricle of the heart 10 by means of electrodes 30 and 28 on lead 14 as well as an atrial pulse generator circuit coupled to the atrium of heart 10 by means of atrial electrodes 20 and 22, located on lead 16. An amplitude/pulse width control 351 is coupled to the output amplifier circuit 340 and a digital controller/timer circuit 330. The amplitude/pulse width control 351 cooperates with the output amplifier circuit 340 to adjust the output amplitude and/or pulse width of signals needed for pacing a patient's heart and for evaluating a heart tissue/pacing lead electrode interface in accordance with the principles of the present invention.

Sense amplifier circuit 360 includes atrial and ventricular sense amplifiers coupled to the atrium and ventricle, respectively, by means of leads 14 and 16. The output circuit 340 and sense amplifier circuit 360 may contain pulse generators and sense amplifiers corresponding to any of those presently employed in commercially marketed cardiac pacemakers. For purposes of explaining the present invention, it will be assumed that the atrial electrodes 20, 22 and the ventricular electrodes 28, 30 are coupled to the atrial and ventricular sense amplifiers and pulse generators, respectively, for pacing and sensing in the bipolar mode.

Sensed atrial depolarizations or P-waves that are confirmed by the atrial sense amplifier (A-event) in response to an A-sense signal are communicated to the digital controller/timer circuit 330 on A-event line 352. Similarly, ventricular depolarizations or R-waves that are confirmed by the ventricular sense amplifier (V-event) in response to a V-sense signal are communicated to the digital controller/timer circuit 330 on V-event line 354. In order to trigger generation of a ventricular pacing or V-pace pulse, digital controller/timer circuit 330 generates a trigger signal on V-trig line 342. Similarly, in order to trigger an atrial pacing or A-pace pulse, digital controller/timer circuit 330 generates a trigger pulse on A-trig line 344.

Control of timing and other functions within the pacing circuit 320 is provided by digital controller/timer circuit 330, which includes a set of timers and associated logic. Digital controller/timer circuit 330 defines the basic pacing or escape interval, which may take the form of an A—A escape interval initiated on atrial sensing (A-event) or pacing (A-pace) and triggering atrial pacing (A-pace) at the expiration thereof or may take the form of a V—V escape interval, initiated on ventricular sensing (V-event) or pacing (V-pace) and triggering ventricular pulse pacing (V-pace) at the expiration thereof. Digital controller/timer circuit 330 similarly defines the A-V delay intervals SAV (Sensed A-V) and PAV (Paced A-V) that commence following a sensed A-event and a delivered A-pace, respectively. The specific values of the intervals defined are controlled by the microcomputer circuit 302 by means of data and control bus 306 from programmed in parameter values and operating modes. Digital controller/timer circuit 330 also controls sensitivity settings of the sense amplifiers 360 by means of sensitivity control 350.

In the embodiment illustrated in FIG. 3, the IPG 26 is provided with a piezoelectric sensor 316 which is intended to monitor patient activity, such that the defined pacing rate (A—A escape interval or V—V escape interval) increases with increased demand for oxygenated blood. Sensor 316 generates electrical signals in response to sensed physical activity which are processed by activity circuit 322 and provided to digital controller/timer circuit 330. Activity circuit 322 and associated sensor 316 may correspond to the circuitry disclosed in U.S. Pat. No. 5,052,388 to Betzold et al. and U.S. Pat. No. 4,428,378 to Anderson et al., each of which is incorporated herein by reference in its entirety. Similarly, the present invention may be practiced in conjunction with alternate types of sensors, such as oxygenation sensors, pressure sensors, pH sensors and respiration sensors, all well known for use in providing rate responsive pacing capabilities. As stated above, the present invention may also be practiced in non-rate responsive pacemakers.

Data transmission to and from the external programmer 40 illustrated in FIG. 2 is accomplished by means of the telemetry antenna 334 and an associated RF transmitter and receiver 332, which serves both to demodulate received downlink telemetry and to transmit uplink telemetry. For example, circuitry for demodulating and decoding downlink telemetry may correspond to that disclosed in U.S. Pat. No. 4,556,063 to Thompson et al. and U.S. Pat. No. 4,257,423 to McDonald et al., while uplink telemetry functions may be provided according to U.S. Pat. No. 5,127,404 to Wyborny et al. and U.S. Pat. No. 4,374,382 to Markowitz, each of which is incorporated herein by reference in its entirety. Uplink telemetry capabilities will typically include the ability to transmit stored digital information as well as real time or stored EGMs of atrial and/or ventricular electrical activity (according to the teaching of the above-cited Wyborny patent), as well as transmission of Marker Channel pulses indicating the occurrence of sensed and paced depolarizations in the atrium and ventricle, as disclosed in the cited Markowitz patent.

In addition, in the context of the present invention, stimulation threshold data from a series of auto-capture test stimulation pace events may be stored in the RAM 310 or the RAM/ROM unit 314 of microcomputer 302 for later telemetry out on command of the programmer 40. This data may be encoded in digital form and transmitted via RF transmitter 332 and antenna 334 to the external programmer 40 for display and/or analysis in the form of atrial and ventricular strength-duration curves, as will be discussed in greater detail hereinbelow.

Crystal oscillator circuit 338 provides the basic timing clock for the pacing circuit 320, while battery 318 provides power. Power-on-reset circuit 336 responds to initial connection of the circuit to the battery for defining an initial operating condition and similarly, resets the operative state of the device in response to detection of a low battery condition. Reference mode circuit 326 generates stable voltage references and currents for the analog circuits within the pacing circuit 320, while analog to digital converter (ADC) and multiplexor circuit 328 digitizes analog signals and voltage to provide real time telemetry for cardiac signals from sense amplifiers 360, for uplink transmission via RF transmitter and receiver circuit 332. Voltage reference and bias circuit 326, ADC and multiplexor 328, power-on-reset circuit 336 and crystal oscillator circuit 338 may correspond to any of those presently used in current marketed implantable cardiac pacemakers.

Microcomputer 302 controls the operational functions of digital controller/timer 330, specifying which timing intervals are employed, and controlling the duration of the various timing intervals, via data and control bus 306. Microcomputer 302 contains a microprocessor 304 and associated system clock 308 and on-processor RAM and ROM chips 310 and 312, respectively. In addition, microcomputer circuit 302 includes a separate RAM/ROM chip 314 to provide additional memory capacity. Microprocessor 304 is interrupt driven, operating in a reduced power consumption mode normally, and awakened in response to defined interrupt events, which may include the A-trig, V-trig, A-event and V-event signals. If the IPG is programmed to a rate responsive mode, the patient's activity level is monitored periodically and the escape interval is adjusted proportionally. A timed interrupt, e.g., every two seconds, may be provided in order to allow the microprocessor 304 to analyze the output of the activity circuit 322 and update the basic escape interval (A—A or V—V) of the IPG.

The illustrated IPG block diagram of FIG. 3 is merely exemplary, and corresponds to the general functional organization of typical multi-programmable microprocessor controlled cardiac pacemakers presently commercially available and well suited for implementing a pacing lead dislodgment methodology according to the principles of the present invention. It is believed that the present invention is most readily practiced in the context of such a device, and that the present invention can therefore readily be practiced using the basic hardware of existing microprocessor controlled dual chamber pacemakers, as presently available, with the invention implemented primarily by means of modifications to the software stored in the ROM 312 of the microcomputer circuit 302. The present invention, however, should not be understood to be limited to a pacemaker having an architecture and functionality as previously discussed with reference to FIGS. 1–3.

By way of example, the medical device depicted in the Figures may be an implantable cardiac pacemaker such as those disclosed in U.S. Pat. No. 5,158,078 to Bennett et al., U.S. Pat. No. 5,312,453 to Shelton et al., or U.S. Pat. No. 5,144,949 to Olson, hereby incorporated herein by reference in their respective entireties. The implantable medical device may also be a pacemaker/cardioverter/defibrillator (PCD), such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless, or U.S. Pat. No. 4,821,723 to Baker et al., all hereby incorporated herein by reference in their respective entireties.

As was discussed in the Background of the Invention, various approaches have been developed for evaluating the heart tissue/pacing lead electrode interface which involve the use of lead impedance. Such approaches are generally capable of detecting only gross levels of degradation of the heart tissue/pacing lead electrode interface, and are typically unable to predict impending failure at this interface. Microdislodgment, for example, is a failure mechanism which may be viewed as a precursor to gross and catastrophic failure of the heart tissue/pacing lead electrode interface.

A pacing lead dislodgment testing approach according to the principles of the present invention provides for the detection of subtle changes occurring at the heart tissue/pacing lead electrode interface. Further, a pacing lead dislodgment testing approach of the present invention exploits blood movement between heart chambers (e.g., atrioventricular (AV) contraction) as a mechanism for mechanically displacing a pacing lead as part of an evaluation of the heart tissue/pacing lead electrode interface. In other words, the mechanical action of the heart is exploited as a mechanism for "wiggling the lead" (i.e., moving the pacing lead and thus the electrode implanted at the heart tissue/pacing lead electrode interface). More particularly, an electrical characteristic of the heart tissue/pacing lead electrode interface is evaluated by measuring pacing threshold values at different points in the cardiac cycle while the pacing lead is subjected to varying degrees of mechanical distension.

Figure 4:
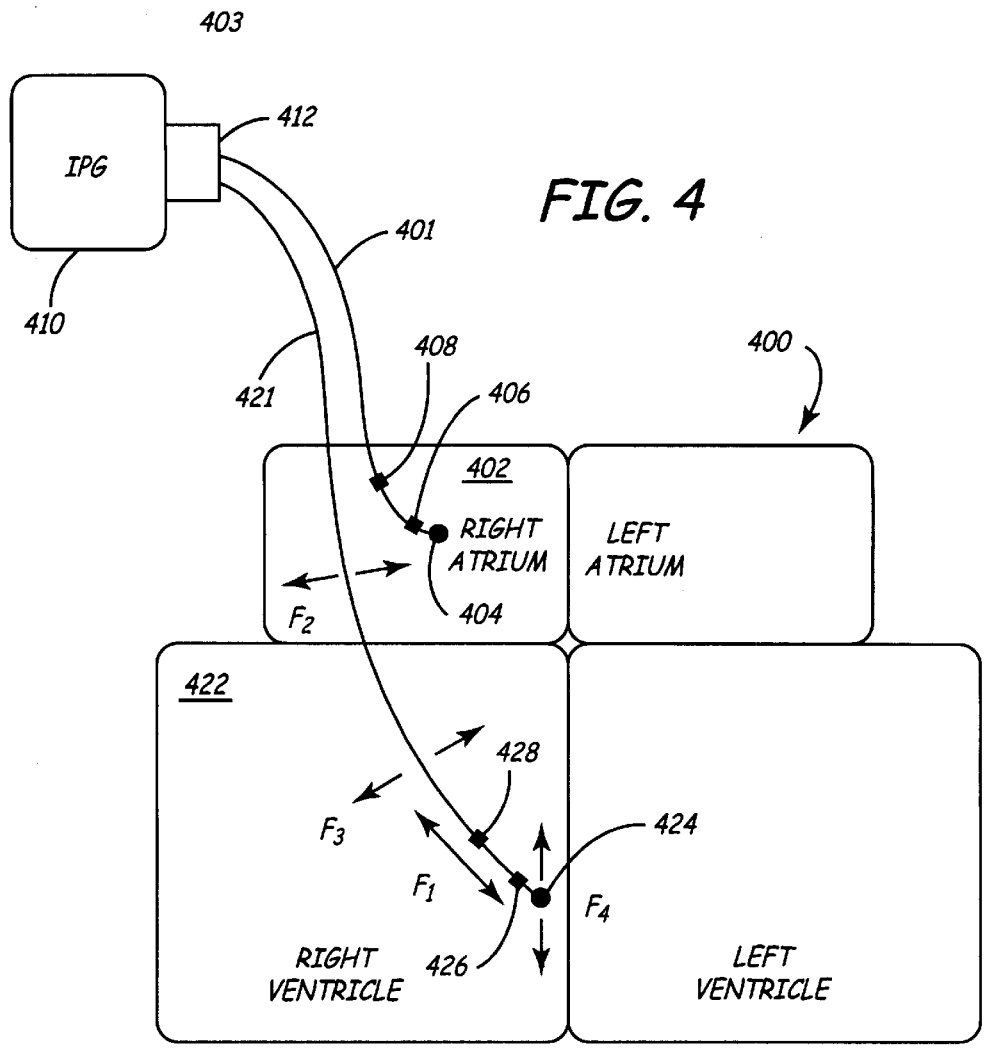
FIG. 4 a generalized depiction of the four chambers of a human heart including, in particular, the right atrium and the right ventricle, with an implantable medical device coupled to pacing leads for implementing a pacing lead dislodgment detection procedure in accordance with the principles of the present invention.

In accordance with a preferred embodiment of the present invention, and with reference to FIG. 4, there is shown a generalized depiction of the four chambers of a human heart 400 including, in particular, the right atrium 402 and the right ventricle 422. Also shown in FIG. 4 is an implantable medical device 403 which, in accordance with this embodiment, incorporates an IPG. IPG 403 includes a connector block 412 to which two pacing leads 401, 421 are connected. An atrial lead 401 extends from connector block 412 to an attachment site 404 on the wall of the right atrium 402. A ventricular pacing lead 421 extends from connector block 412 to an attachment site 424 on the wall of the right ventricle 422.

It is understood that each of the atrial and ventricular pacing leads 401, 421, in accordance with one embodiment, may include at least two conductors terminated by a ring and tip electrode. In the case of a unipolar implementation, the atrial and ventricular pacing leads 401, 421 would each include a single conductor. In the case of a bipolar implementation, atrial lead 401 includes a ring electrode 408 and a tip electrode 406. Tip electrode 406 is shown attached to attachment site 404 of right atrium 402 to define an atrial electrode-to-atrial heart tissue interface. Electrodes 406 and 408 are used both to sense atrial depolarizations (i.e., P-waves) and to deliver atrial pacing pulses. It is noted that atrial pacing pulses may be delivered between electrodes 406 and 408 in a bipolar pacing mode or between tip electrode 406 and the housing of IPG 410 in a unipolar pacing mode. Sensing of P-waves may occur between electrodes 406 and 408 in a bipolar sensing mode or between either of electrode 406 or 408 and the IPG housing in a unipolar sensing mode.

Similarly, ventricular lead 421 includes a ring electrode 428 and a tip electrode 426 according to this embodiment. Tip electrode 426 is shown attached to attachment site 424 of right ventricle 422 to define a ventricular electrode-to-ventricular heart tissue interface. Electrodes 426 and 428 are used both to sense ventricular depolarizations (i.e., R-waves) and to deliver ventricular pacing pulses. Ventricular pacing pulses may be delivered between electrodes 426 and 428 in a bipolar pacing mode or between tip electrode 426 and the housing of IPG 410 in a unipolar pacing mode. Sensing of R-waves may occur between electrodes 426 and 428 in a bipolar sensing mode or between either of electrode 426 or 428 and the IPG housing in a unipolar sensing mode.

FIG. 4 further illustrates various forces that act upon the pacing leads 401 and 421 as a result of flexion of the heart walls during A & V contraction (i.e., "wiggling the lead"). For purposes of simplicity of explanation, the various forces acting on the ventricular pacing lead 421 and ventricular tip electrode-heart tissue interface 424 are generally depicted as forces $F_1$, $F_2$, $F_3$, and $F_4$, it being understood that these forces are provided and discussed for purposes of illustration only.

When the right atrium 402 contracts followed by contraction of the right ventricle 422 in response thereto, the ventricular pacing lead 421 is subject to positional shifting due to forces produced during an A & V contraction. The force, $F_3$, produced by the right ventricle 422, for example, subjects the ventricular pacing lead 421 to torquing forces due to the relative distance between force $F_3$ acting on ventricular pacing lead 421 and the fixed ventricular tip electrode-heart tissue interface 424.

Similarly, the force, $F_2$, produced by the right atrium 402 also subjects the ventricular pacing lead 421 to torquing forces. The positional shifting or wiggling of the ventricular lead 421 results in the production of various forces, depicted generally as force $F_4$, at the ventricular tip electrode-heart tissue interface 424. It is noted that the ventricular lead 421 may be subject to both tensile and compressive forces, depicted as force $F_1$, due to its spring-like configuration.

A micro-dislodgment testing approach consistent with the principles of the present invention takes advantage of the positional shifting of the ventricular lead 421 by characterizing the ventricular tip electrode-heart tissue interface 424 and monitoring for a change in a ventricular tip electrode-heart tissue interface characteristic while the ventricular pacing lead 421/tip electrode 426 is subjected to positional shifting by blood movement during A & V contractions. Concern about the ventricular tip electrode-heart tissue interface is warranted if an appreciable change in the ventricular tip electrode-heart tissue interface characteristic is detected.

In accordance with a preferred embodiment, the pacing threshold of a patient is measured at varying degrees of mechanical distension of the pacing lead, which correspond to varying levels of mechanical stress imparted to the ventricular tip electrode-heart tissue interface 424. It is understood that a patient's pacing threshold represents the minimum energy required to stimulate the heart so as to produce a cardiac contraction (i.e., "capture") in direct response to the application of an electrical stimulation signal. By measuring the patient's pacing threshold at different points in the patient's cardiac cycle, subtle and heretofore undetectable changes at the heart tissue/pacing lead electrode interface (e.g., micro-dislodgment), including intermittent changes, may be detected. Moreover, such changes at the heart tissue/pacing lead electrode interface may be quantified.

Figure 5:
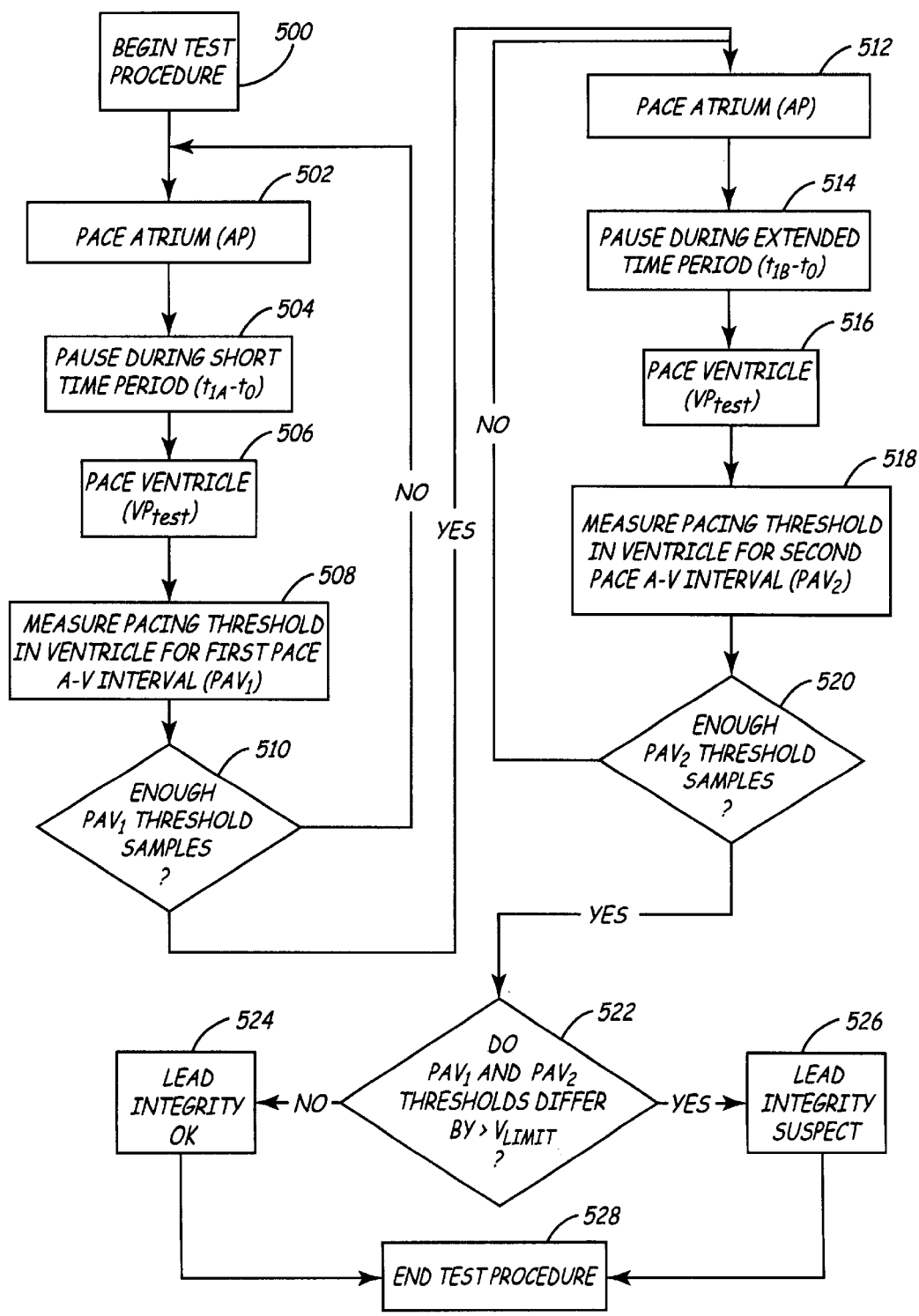
FIG. 5 is a flow diagram of various process steps associated with a pacing lead micro-dislodgment testing methodology in accordance with an embodiment of the present invention.

Turning now to FIG. 5, there is shown in flow diagram form various process steps associated with a pacing lead micro-dislodgment testing methodology in accordance with an embodiment of the present invention. A micro-dislodgment testing approach according to this embodiment involves the use of a set of time-variant test PAV intervals during which pacing threshold measurements are taken.

PAV intervals of increased duration, up to a certain point, are associated with increased levels of mechanical distension of the pacing lead, and, thus, increased disturbance of the heart tissue/pacing lead electrode interface. Measuring pacing thresholds at two or more time-separated PAV intervals provides for a direct evaluation of the heart tissue/pacing lead electrode interface when subjected to varying levels of mechanical disturbance.

Prior to initiating 500 the micro-dislodgment testing procedure depicted in FIG. 5, a patient's paced A-V conduction time is measured in a manner known in the art. A test pace A-V interval employed in the micro-dislodgment testing procedure of the present invention must be less than the patient's paced A-V conduction time.

Figure 7:
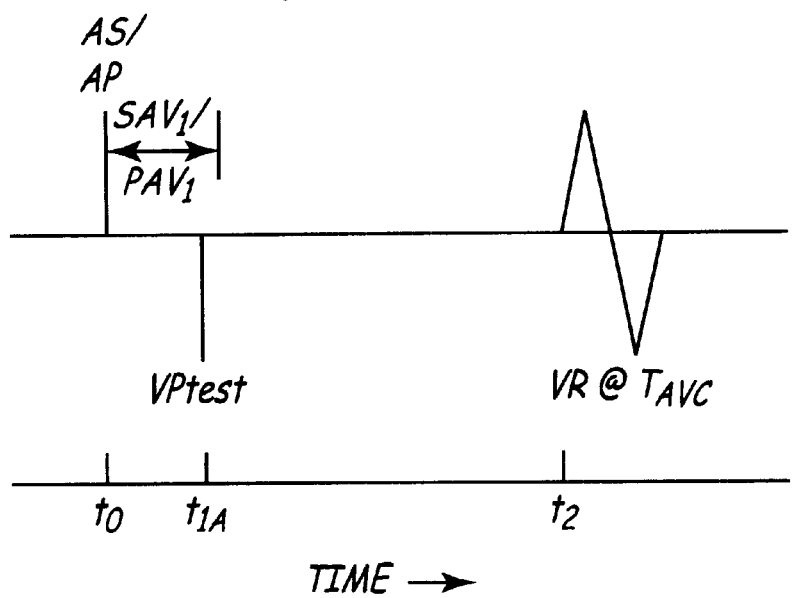
FIGS. 7 and 8 are timing diagrams illustrating the generation/sensing of cardiac signals associated with a pacing lead micro-dislodgment testing methodology in accordance with the principles of the present invention.

After determining the patient's A-V conduction time, the micro-dislodgment testing procedure is initiated 500 by pacing 502 the atrium, as is shown in FIG. 7 as an atrium pace (AP) event at time $t_0$. After a relatively short time delay 504 after the atrium pace event 502, but prior to any appreciable contraction of the right ventricle, shown as delay time period $t_{1A}-t_0$, the right ventricle is paced 506, shown as a ventricle test pace event, $VP_{test}$, at time $t_{1A}$ in FIG. 7. A pacing threshold measurement is taken 508 using the tip electrode embedded in the right ventricle wall (e.g., ventricular tip electrode-heart tissue interface 424 shown in FIG. 4).

The pacing threshold measurement for the first PAV interval, $PAV_1$, represents a pacing threshold measurement associated with a minimal level of pacing lead/electrode movement imparted by the blood ejected by the atrium into the right ventricle. The first PAV interval, $PAV_1$, is typically about 50 ms in duration, but may range between about 10 ms to about 110 ms in duration. It is considered desirable to perform steps 502–510 a number of times in order to obtain a stable first PAV interval pacing threshold value.

Figure 8:
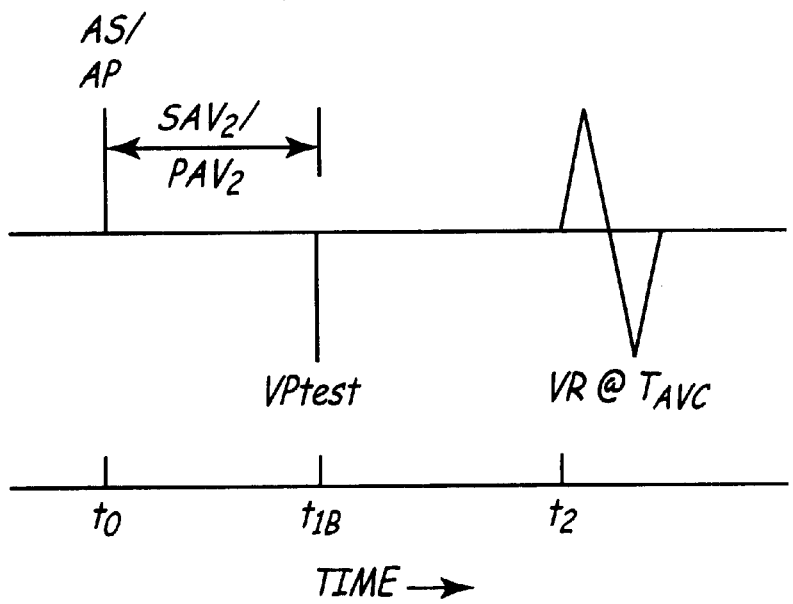

The micro-dislodgment testing procedure depicted in FIG. 5 continues by obtaining a stable pacing threshold measurement for a second PAV interval, $PAV_2$, of greater duration relative to the first PAV interval, $PAV_1$. The atrium is paced 512, as is shown in FIG. 8 as an atrium pace (AP) event at time $t_0$, followed by a time delay period 514, shown as delay time period $t_{1B}$—$t_0$. The delay time period, $t_{1B}$–$t_0$, is selected such that an atrial contraction has completed and an appreciable amount of right ventricular filling has occurred. The right ventricle is then paced 516, shown as a ventricle test pace event, $VP_{test}$, at time $t_{1B}$ in FIG. 8.

A pacing threshold measurement is then taken 518. The pacing threshold measurement for the second PAV interval, $PAV_2$, represents a pacing threshold measurement associated with an increased level of pacing lead/electrode movement relative to that associated with the first PAV interval, $PAV_1$. The second PAV interval, $PAV_2$, is typically about 150 ms to about 250 ms in duration, but may range between about 100 ms to about 400 ms in duration. It is considered desirable to perform steps 512–520 a number of times in order to obtain a stable second PAV interval pacing threshold value. It will be appreciated that pacing threshold values may be obtained at any number of PAV intervals, and that such PAV intervals may be of any duration less than the time defined between an atrial pace event and a ventricular beat resulting from that atrial pace event associated with A-V conduction, shown as VR @ $T_{AVC}$ in FIGS. 7 and 8 occurring at time $t_2$. (e.g., R-wave shown at time $t_2$).

The pacing threshold value or averaged value obtained for the first PAV interval, $PAV_1$, is compared 522 to the pacing threshold value or averaged value obtained for the second PAV interval, $PAV_2$. If the threshold values for the first and second PAV intervals, $PAV_1$ and $PAV_2$, are substantially equal or within an acceptable tolerance band, then the condition of the heart tissue/pacing lead electrode interface is considered nominal 524. If, however, the threshold values for the first and second PAV intervals, $PAV_1$ and $PAV_2$, differ by more than a preestablished maximum value, such as a preestablished voltage limit $V_{limit}$, then the condition of the heart tissue/pacing lead electrode interface is suspect 526. The micro-dislodgment testing procedure then terminates 528.

It is believed that a difference between pacing threshold values for the first and second PAV intervals, $PAV_1$ and $PAV_2$, in excess of 0.5 volts (i.e., $V_{limit}$) is indicative of a problematic heart tissue/pacing lead electrode interface. The value of 0.5 V represents a clinically significant value which a physician would likely consider worrisome or indicative of a problem at the heart tissue/pacing lead electrode interface. It is believed that more tailored values of $V_{limit}$ may be developed empirically through use of clinical studies and through use of historical data developed for a particular patient or patient profile.

Alternatively, the threshold values for the intervals $PAV_1$ and $PAV_2$ may be expressed in the form of a threshold ratio, such as the ratio of $Thresh_{PAV2}/Thresh_{PAV1}$. Under nominal conditions, the threshold ratio should be about 1 (i.e., substantially equal), plus or minus a reasonable tolerance. Threshold ratios that deviate beyond 1 (i.e., nominal conditions) by a preestablished maximum allowable deviation value, such as by 15% or 20% for example, indicate the existence of a suspect heart tissue/pacing lead electrode interface.

It is understood that the values of the threshold limit, $V_{limit}$, and threshold ratio may be modified over time for a particular patient or patent profile, and may further be adjusted to provide for greater or lesser degrees of micro-dislodgment detection resolution. For example, values of $V_{limit}$ may range between 0.2 V and 0.7 V, and the preestablished maximum allowable deviation value may range between 5% to 50%. It will be appreciated that the general procedures described herein for detecting lead dislodgment may be implemented within the constraints imposed by any of the mechanical heart contraction cycles.

Figure 6:
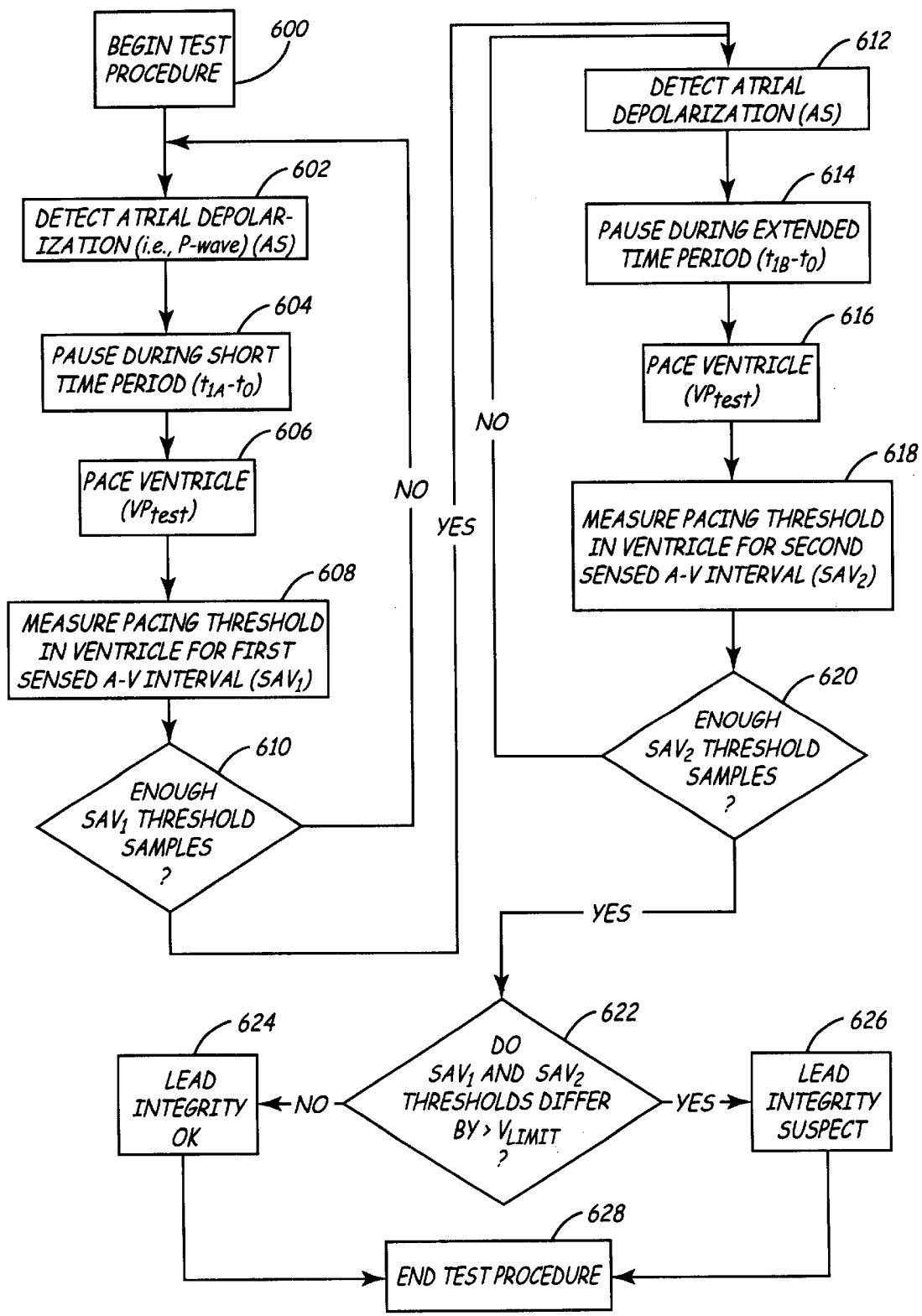
FIG. 6 is a flow diagram of various process steps associated with a pacing lead micro-dislodgment testing methodology in accordance with another embodiment of the present invention.

With reference to FIG. 6, there is depicted in flow diagram form various process steps associated with a pacing lead micro-dislodgment testing methodology in accordance with another embodiment of the present invention. A micro-dislodgment testing approach in accordance with this embodiment involves the use of a set of time-variant test sensed A-V (SAV) intervals during which pacing threshold measurements are taken.

After determining the patient's A-V conduction time, the micro-dislodgment testing procedure is initiated 600 by detecting 602 an atrial depolarization event (i.e., P-wave), as is shown in FIG. 7 as an atrium sense (AS) event at time $t_0$. After a relatively short time delay 604 after the atrium sense event 602, but prior to any appreciable contraction of the right ventricle, shown as delay time period $t_{1A}$–$t_0$, the right ventricle is paced 606, shown as a ventricle test pace event, $VP_{test}$, at time $t_{1A}$ in FIG. 7. A pacing threshold measurement is then taken 608. The pacing threshold measurement typically involves the application of several stimuli and detection windows as is known in the art, from which the pacing threshold measurement is determined.

The pacing threshold measurement for the first SAV interval, $SAV_1$, represents a pacing threshold measurement associated with a minimal level of pacing lead/electrode movement. The first SAV interval, $SAV_1$, is typically about 50 ms in duration, but may vary as discussed above. Steps 602–610 should be performed a number of times in order to obtain a stable first SAV interval pacing threshold value.

A stable pacing threshold measurement for a second SAV interval, $SAV_2$, of greater duration relative to the first SAV interval, $SAV_1$, is then determined. An atrium sense (AS) event is detected 612, as is shown in FIG. 8 occurring at time $t_0$, followed by a time delay period 614, shown as delay time period $t_{1B}$–$t_0$. Again, the delay time period, $t_{1B}$–$t_0$, is selected such that an atrial contraction has completed and an appreciable amount of right ventricle contraction has occurred. The right ventricle is then paced 616, shown as a ventricle test pace event, $VP_{test}$, at time $t_{1B}$ in FIG. 8.

A pacing threshold measurement is then taken 618. The second SAV interval, $SAV_2$, is typically about 150 ms to about 250 ms in duration, but may vary as previously discussed. It is considered desirable to perform steps 612–620 a number of times in order to obtain a stable second SAV interval pacing threshold value. It will be appreciated that pacing threshold values may be obtained at any number of SAV intervals, and that such SAV intervals may be of any duration less than the time defined between an atrial pace event and a ventricular refractory event associated with A-V conduction, shown as VR @ $T_{AVC}$ in FIGS. 7 and 8.

The pacing threshold values obtained for the first SAV interval, $SAV_1$, is compared 622 to the pacing threshold obtained for the second SAV interval, $SAV_2$. If the threshold values for the first and second SAV intervals, $SAV_1$ and $SAV_2$, are substantially equal or within an acceptable tolerance band, then the condition of the heart tissue/pacing lead electrode interface is considered nominal 624. If, however, the threshold values for the first and second SAV intervals, $SAV_1$ and $SAV_2$, differ by more than a preestablished maximum value, such as a preestablished voltage limit $V_{limit}$, then the condition of the heart tissue/pacing lead electrode interface is suspect 626. The micro-dislodgment testing procedure then terminates 628.

As in the case of PAV threshold values, it is believed that a to difference between threshold values for the first and second SAV intervals, $SAV_1$ and $SAV_2$, in excess of 0.5 volts (i.e., $V_{limit}$) is indicative of a suspect heart tissue/pacing lead electrode interface, although the value of $V_{limit}$ may vary as previously discussed above. Alternatively, threshold ratios, such as the ratio of $Thresh_{SAV2}/Thresh_{SAV1}$, that deviate from 1 by a preestablished deviation amount, such as by 15% or 20%, indicate the existence of a suspect heart tissue/pacing lead electrode interface, although these percentages may vary as previously discussed above.

It will be appreciated that a micro-dislodgment detection methodology consistent with the principles of the present invention may be implemented using any of a number of capture detection techniques, and, more particularly, the pacing threshold values may be obtained using a variety of approaches. By way of example, the techniques disclosed in the following U.S. Patents may be employed: U.S. Pat. No. 5,601,615 to Markowitz et al.; U.S. Pat. No. 5,702,427 to Ecker et al.; U.S. Pat. No. 5,713,933 to Condie et al.; U.S. Pat. Nos. 5,861,012 and 5,480,414 both to Stroebel et al.; U.S. Pat. No. 5,350,410 to Kleks et al.; U.S. Pat. No. 5,718,720 to Prutchi et al.; U.S. Pat. Nos. 5,222,493 and 5,476,487 both to Sholder; U.S. Pat. No. 4,969,460 to Callaghan et al.; U.S. Pat. Nos. 5,697,956 and 5,766,229 both to Bornzin; U.S. Pat. No. 5,411,533 to Dubreuil et al.; and U.S. Pat. No. 5,549,652 to McClure et al.; all of which are hereby incorporated by reference in their respective entireties.

Additionally, pacing threshold values may be obtained using a signal developed at the appropriate sense output of the sense amplifier(s), such a sense amplifier(s) 360 shown in FIG. 3. Alternatively, pacing threshold values may be derived from manual observation of an EGC readout, such as a readout produced using an external programmer (e.g., commercially available Medtronic Model 9790 programmer) that communicates with the IPG. Pacing threshold values may also be obtained through detection of an escape interval or an intrinsic R-wave using a known capture detection technique, such as those disclosed in previously referenced U.S. Pat. No. 5,601,615 to Markowitz et al.

Figure 9:
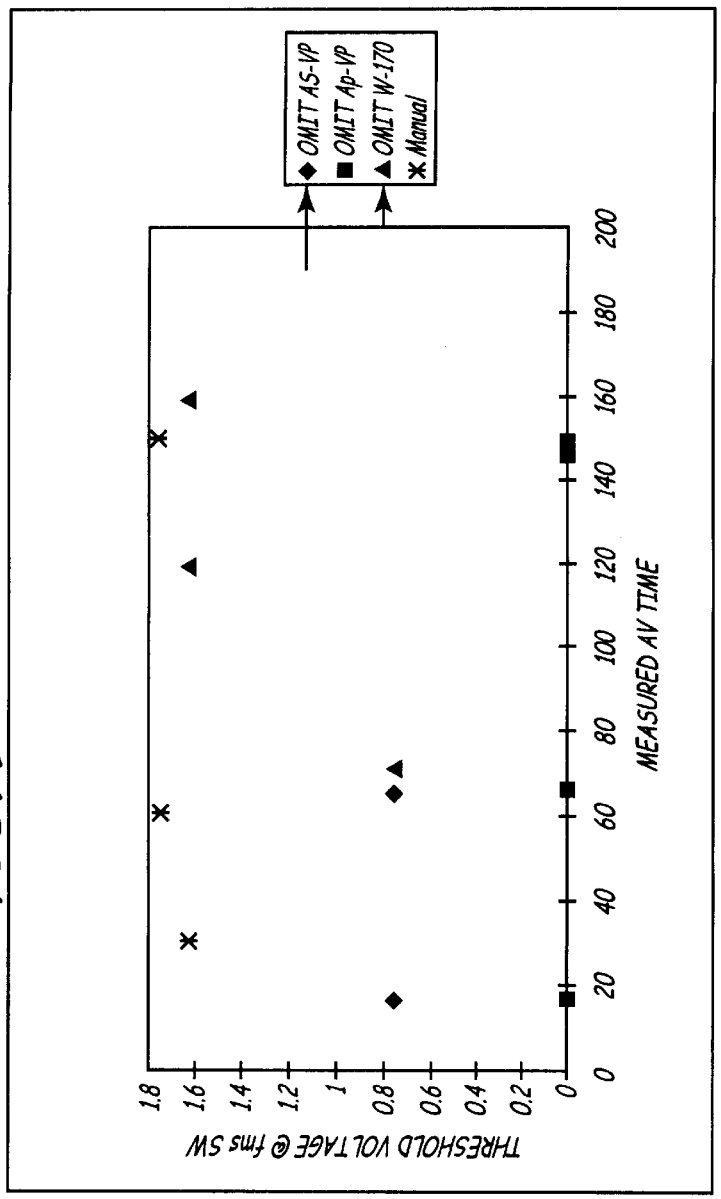
FIG. 9 shows tabulated and plotted clinical data that verifies the efficacy of a micro-dislodgment detection technique consistent with the principles of the present invention.
Figure 9:
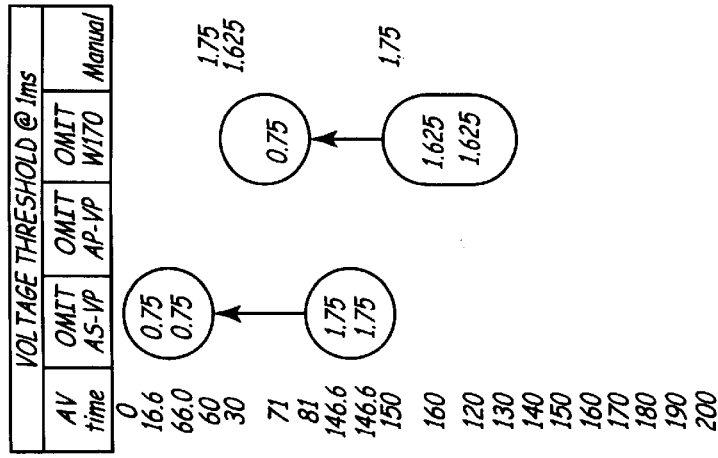

Turning now to FIG. 9, there is shown numerical and plotted data that demonstrates the efficacy of a micro-dislodgment detection technique consistent with the principles of the present invention. The data shown and plotted in FIG. 9 represents actual clinical data that was developed for a patient experiencing problems consistent with those associated with a suspect lead/electrode attachment condition. Conventional lead/electrode attachment evaluation techniques used on this patient, however, failed to detect a lead/electrode attachment problem.

A micro-dislodgment detection technique of the present invention, however, successfully and unambiguously detected the presence of a suspect lead/electrode attachment problem. The first column of pacing threshold data tabulated data in FIG. 9 and associated with AS-VP cycles shows a first threshold value of 0.75 V at a first SAV interval, $SAV_1$, of 16.6 ms and a second threshold value of 0.75 V at a second SAV interval, $SAV_2$, of 66.6 ms. It can be seen that the pacing threshold values are equivalent at intervals $SAV_1$ and $SAV_2$. The threshold values for intervals $SAV_1$ and $SAV_2$ are shown by respective diamond symbols in the corresponding chart of FIG. 9. FIG. 9 further shows a second and third threshold value of 1.75 V at a respective third and fourth SAV interval, $SAV_3$ and $SAV_4$, of 146.6 ms. Again, it can be seen that the pacing threshold values are equivalent at intervals $SAV_3$ and $SAV_4$, which are of equal duration.

A comparison of the pacing threshold values obtained at intervals $SAV_1/SAV_2$ with those obtained at intervals $SAV_3/SAV_4$ reveals a threshold voltage difference of 1 V (i.e., 1.75 V−0.75 V =1.0 V). Using a preestablished voltage limit, $V_{limit}$, of 0.5 V, it can be seen that the threshold voltage difference of 1 V is greater than the preestablished voltage limit, $V_{limit}$ (i.e., 1.0 V>$V_{limit}$ of 0.5 V). This excessively high threshold voltage difference between two pacing threshold values measured at PAVs of unequal duration indicates that the condition of the heart tissue/pacing lead electrode interface is suspect. Expressed in terms of a pacing threshold ratio, it can be seen that this ratio is given as $Thresh_{SAV2}/Thresh_{SAV1}$=1.75 V/0.75 V≈2.33. A deviation of $Thresh_{SAV2}$ relative to $Thresh_{SAV1}$ of about 233% well exceeds the preestablished maximum allowable deviation value of, for example, 15% or 20%, again indicating a suspect heart tissue/pacing lead electrode interface.

It will be appreciated that a micro-dislodgment detection methodology in accordance with the principles of the present invention may be performed by or in conjunction with a pacing system analyzer, such as an external programmer of the type previously described, during the implantation procedure to assure the physician of proper lead placement. A micro-dislodgment detection methodology according to the present invention may also be performed by or in conjunction with an IPG before releasing the patient to assure that the lead has remained in its proper implanted position, and may subsequently provide for continuous monitoring of the lead/electrode implant interface to provide additional diagnostic information, such as in cases in which the patient falls or is involved in a traffic accident or other mishap which could be potentially problematic. In such cases, heart tissue/pacing lead electrode interface condition data may be produced by the IPG on a periodic, continuous, or as-needed basis and stored in the IPG for subsequent uplinking to an external programmer or other receiving system for evaluation by a physician.

The foregoing description of the various embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

What is claimed is:

1. A method of detecting micro-dislodgment at a heart tissue/pacing lead electrode interface, comprising:

measuring a first pacing threshold parameter at a first time in a patient's cardiac cycle;

measuring a second pacing threshold parameter at a second time in the patient's cardiac cycle, the second time being different from the first time; and detecting micro-dislodgment at the heart tissue/pacing lead electrode interface using the first and second pacing threshold parameters.

2. The method of claim 1, wherein each of the first and second pacing threshold parameters is a pacing threshold voltage.

3. The method of claim 1, wherein each of the first and second pacing threshold parameters is a pacing threshold pulse width.

4. The method of claim 1, wherein detecting micro-dislodgment comprises comparing a difference between the first pacing threshold parameter and the second pacing threshold parameter to a preestablished maximum allowable deviation value.

5. The method of claim 4, wherein the preestablished maximum allowable deviation value is a voltage ranging from about 0.2 volts to about 2 volts.

6. The method of claim 1, wherein detecting micro-dislodgment comprises computing a ratio of the first pacing threshold parameter relative to the second pacing threshold parameter and comparing the computed ratio to a preestablished maximum allowable deviation value.

7. The method of claim 6, wherein the preestablished maximum allowable deviation value is a percentage ranging from about 5% to about 50%.

8. The method of claim 1, wherein:
measuring the first pacing threshold parameter comprises measuring the first pacing threshold parameter after initiation of an atrial contraction but prior to any appreciable amount of ventricular contraction; and
measuring the second pacing threshold parameter comprises measuring the second pacing threshold parameter after initiation of an atrial contraction and after an appreciable amount of ventricular contraction.

9. The method of claim 1, wherein:
measuring the first pacing threshold parameter comprises measuring the first pacing threshold parameter after a delay of up to about 110 ms subsequent to initiation of an atrial contraction; and
measuring the second pacing threshold parameter comprises measuring the second pacing threshold parameter after a delay of about 100 ms to about 400 ms subsequent to initiation of an atrial contraction.

10. The method of claim 1, further comprising performing the respective measuring steps and the detecting step using an external programmer and an implantable medical device.

11. The method of claim 1, further comprising performing the respective measuring steps and the detecting step during implantation of a pacing lead electrode at the heart tissue/pacing lead electrode interface.

12. The method of claim 1, further comprising performing the respective measuring steps and the detecting step solely by use of an implantable medical device comprising a pulse generator.

13. The method of claim 1, further comprising performing the respective measuring steps and the detecting step using an implantable medical device while the patient of ambulatory.

14. The method of claim 1, further comprising storing data indicative of the detected micro-dislodgment.

15. The method of claim 14, further comprising reading out the stored data indicative of the detected micro-dislodgment.

16. A method of detecting changes at a heart tissue/pacing lead electrode interface, comprising:
stimulating the right atrium to contract using an atrium pace signal or sensing a right atrium contraction;
measuring a first pacing threshold parameter in the right ventricle prior to any appreciable contracting of the right ventricle;
repeating stimulating the right atrium to contract using an atrium pace signal or sensing a right atrium contraction;
measuring a second pacing threshold parameter in the right ventricle during appreciable contracting of the right ventricular; and
determining a change at the heart tissue/pacing lead electrode interface using the first and second pacing threshold parameters.

17. The method of claim 16, wherein each of the first and second pacing threshold parameters is a pacing threshold voltage.

18. The method of claim 16, wherein each of the first and second pacing threshold parameters is a pacing threshold pulse width.

19. The method of claim 16, wherein:
measuring the first pacing threshold parameter comprises measuring the first pacing threshold parameter subsequent to a first delay period of up to about 110 ms following the right atrium contraction; and
measuring the second pacing threshold parameter comprises measuring the second pacing threshold parameter subsequent to a second delay period of about 100 ms to about 400 ms following the right atrium contraction.

20. The method of claim 16, wherein detecting micro-dislodgment comprises comparing a difference between the first pacing threshold parameter and the second pacing threshold parameter to a preestablished maximum allowable deviation value.

21. The method of claim 20, wherein the preestablished maximum allowable deviation value is a voltage ranging from about 0.2 volts to about 2 volts.

22. The method of claim 16, wherein detecting micro-dislodgment comprises computing a ratio of the first pacing threshold parameter relative to the second pacing threshold parameter and comparing the computed ratio to a preestablished maximum allowable deviation value.

23. The method of claim 22, wherein the preestablished maximum allowable deviation value is a percentage ranging from about 5% to about 50%.

24. The method of claim 16, further comprising performing the respective measuring steps and the detecting step using an external programmer and an implantable medical device.

25. The method of claim 16, further comprising performing the respective measuring steps and the detecting step during implantation of a pacing lead electrode at the heart tissue/pacing lead electrode interface.

26. The method of claim 16, further comprising performing the respective measuring steps and the detecting step solely by use of an implantable medical device comprising a pulse generator.

27. The method of claim 16, further comprising performing the respective measuring steps and the detecting step using an implantable medical device while the patient of ambulatory.

28. The method of claim 16, further comprising storing data indicative of the detected change at the heart tissue/pacing lead electrode interface.

29. The method of claim 28, further comprising reading out the stored data indicative of the detected change at the heart tissue/pacing lead electrode interface.

30. An apparatus for detecting micro-dislodgment at a heart tissue/pacing lead electrode interface, comprising:

an implantable medical device including a pulse generator;

a first pacing lead comprising a first electrode adapted for implantation in a right atrium of a heart;

second pacing lead comprising a second electrode adapted for implantation in a right ventricle of the heart; and a microprocessor that determines an occurrence of micro-dislodgment at the second electrode/right ventricle interface using a first pacing threshold parameter, determined for the right ventricle prior to any appreciable contracting of the right ventricle, and a second pacing threshold parameter, determined for the right ventricle during appreciable contracting of the right ventricular.

31. The apparatus of claim 30, wherein each of the first and second pacing threshold parameters is a pacing threshold voltage.

32. The apparatus of claim 30, wherein each of the first and second pacing threshold parameters is a pacing threshold pulse width.

33. The apparatus of claim 30, wherein:

the microprocessor determines the first pacing threshold by determining the first pacing threshold parameter subsequent to a first delay period of up to about 110 ms following a right atrium contraction; and the microprocessor determines the second pacing threshold parameter by determining the second pacing threshold parameter subsequent to a second delay period of about 100 ms to about 400 ms following the right atrium contraction.

34. The apparatus of claim 30, wherein the microprocessor determines the occurrence of micro-dislodgment by comparing a difference between the first pacing threshold parameter and the second pacing threshold parameter to a preestablished maximum allowable deviation value.

35. The apparatus of claim 34, wherein the preestablished maximum allowable deviation value is a voltage ranging from about 0.2 volts to about 2 volts.

36. The apparatus of claim 30, wherein the microprocessor determines the occurrence of micro-dislodgment by computing a ratio of the first pacing threshold parameter relative to the second pacing threshold parameter and comparing the computed ratio to a preestablished maximum allowable deviation value.

37. The apparatus of claim 36, wherein the preestablished maximum allowable deviation value is a percentage ranging from about 5% to about 50%.

38. The apparatus of claim 30, wherein the microprocessor is provided in the implantable medical device.

39. The apparatus of claim 38, wherein the microprocessor stores data indicative of the detected occurrence of micro-dislodgment in a memory provided in the implantable medical device and coordinates transfer of the stored data from the memory to an external programmer.

40. The apparatus of claim 30, wherein the microprocessor is provided in an external programmer.

* * * * *